United States Patent [19]

Milly

[11] Patent Number: 5,137,830
[45] Date of Patent: Aug. 11, 1992

[54] POST-COMPRESSION METHOD OF MEASURING SOIL GAS CONCENTRATION AND EMISSION

[75] Inventor: George H. Milly, Middletown, Md.

[73] Assignee: Quadrel Research Corporation, Middletown, Md.

[21] Appl. No.: 308,283

[22] Filed: Feb. 9, 1989

[51] Int. Cl.$^5$ ............................................. G01N 33/24
[52] U.S. Cl. ........................................ 436/25; 436/32; 436/139; 436/81; 436/122; 367/60
[58] Field of Search .................... 436/32, 29, 25, 139, 436/81, 122; 367/60

[56] References Cited

PUBLICATIONS

Klusman, Ronald W., Jaacks, Jeffrey A.; "Environmental influences upon Mercury, radon, and helium concentrations in soil gases at a site near Denver, Colo." J. Geochem Explor 27(3) 259–280 See CAS abstract #59851e.

Primary Examiner—James C. Housel
Assistant Examiner—Thomas E. Daley
Attorney, Agent, or Firm—David H. Semmes

[57] ABSTRACT

Measuring of soil gas flux. Particularly a method of measuring soil gas concentration and emission flux during a period of post-compression of the earth's crust. The method includes observing gravitational acceleration on the surface of the earth, as defined by crustal tension and compression and as induced by the Sun and Moon, compensating for variation in acceleration due to geographic location of said observing, locating said crustal tension in the form of a bulge on the surface of the earth, then post-compression measuring of soil gas concentration and emission flux rate during both the long term (approximately 1 to 10 days) and short term (approximately 1 to 8 hours) of maximum soil gas emission.

17 Claims, 7 Drawing Sheets

EFFECT OF GRAVITATIONAL FORCE ON GEOID DISTORTION AND CRUSTAL DISPLACEMENT.

① SMOOTH CURVE - VERTICAL COMPONENT OF GRAVITATIONAL ACCELERATION VECTOR
② IRREGULAR CURVE - RADON EMISSION FLUX RATE

N = NOON, GREENWICH MEAN TIME
M = MIDNIGHT

THREE-DAY TIME SERIES OF EMISSION FLUX RATE AND GRAVITATIONAL ACCELERATION INTENSITY

POST-COMPRESSION METHOD OF MEASURING SOIL GAS CONCENTRATION AND EMISSION

BACKGROUND OF THE INVENTION

1. Field of the Invention

Method of measuring soil gas emanation. Particularly a method of measuring both soil gas concentration and emission flux as an aid to oil and gas exploration, minerals exploration, evaluation of polluted sources and the like.

2. Description of the Prior Art

Introduction

The present method of measuring said gas concentrations and emissions enables the control of planning and scheduling of soil gas and atmospheric sampling as a means of geological and geophysical exploration and evaluation, and of detecting and assessing buried natural and anthropogenic substances by reference to natural geophysical phenomena. More specifically, this invention enables an enhanced measuring of soil gas concentrations and emission flux rates, with favorable and unfavorable periods being delineated upon the calculation of the curve of variation of earth tidal forces, and the empirically determined relationship of soil gas concentration and emission flux rate to the tidal forces. The novelty and utility of the invention in a variety of applications is discussed below. For many years various kinds of measurements have been made based on soil gases occurring near or at the surface of the earth and in the atmosphere as a means of detecting and otherwise characterizing source materials buried below the surface and from which such gases arise. Several examples may be cited.

Oil and Gas Exploration

In the oil and gas industry, geological exploration has included detection of hydrocarbons arising from accumulations at depth. In the early days of oil exploration, visible seepage of liquid oil out of the earth enabled detection of deposits near the surface. Later, more sensitive seep detection techniques were employed based on the upward migration of gases arising from volatile components of deeper deposits. Direct Techniques of "micro-seep" detection are based on the hydrocarbons arising from the source deposit itself; indirect techniques are based on non-hydrocarbon gases that may be associated with the deposit, e.g. a radon halo or anomalous concentrations of helium.

Direct techniques have received the most attention and include:

a) microbiological methods based on certain microorganisms that thrive on hydrocarbons that have migrated to the surface (G. G. Soli, "Microorganisms and Geochemical methods of Oil Prospecting", Bulletin of Amer. Assn. of Petroleum Geologists, v. 41, no. 1, pp. 134–40, January 1957; Stravinski, "Microbiological Method of Prospecting for Oil", World Oil, v. 141, no. 6, pp. 104, 106, 109–110, November 1955); and b) the development of certain carbonates formed upon hydrocarbon exposure that can be detected by controlled thermal cycling and monitoring the evolved carbon dioxide from near-surface soil samples (E. McDermott, U.S. Pat. No. 2,590,113, Geochemical Prospecting).

Methods (a) and (b) involve long term exposures to hydrocarbon gases thereby providing stable averaging. However, these techniques are subject to specific near surface characteristics and to important logistic disadvantages: complex analytical techniques, and resultant delays in obtaining results, important to the conduct of grass roots exploration; and possible non-specificity of the method with respect to hydrocarbon sources. Further, these methods do not identify individual hydrocarbons or their relative proportions.

The most frequently employed and accepted gas tracer methods involve direct measurement of the hydrocarbons in soil gas in order to avoid the difficulties cited above. The gas sample is generally obtained by drawing air from a sealed off short drill hole into a collecting medium, or by aspirating soil gas through a metal probe driven several feet into the ground. The collected samples are then analyzed for specific hydrocarbons associable with a source deposit, e.g. a series of low molecular weight alkanes or alkenes and various aromatic compounds. Parallel applications involve sampling the atmosphere (G. H. Milly, U.S. Pat. No. 3,734,489) or the ocean bottom (G. J. Demaison and I. R. Kaplan, U.S. Pat. No. 4,659,675) into which the hydrocarbons have emanated. It is relevant to the present invention as discussed further below that these more generally employed direct soil gas techniques provide nearly instantaneous snapshots in time of the hydrocarbon concentration although, as we shall show, the concentration typically fluctuates widely over short periods of time; and conventional soil gas surveys pursuant to the usual grid or fence sampling plan are accomplished with temporally sequential measurements. The resultant asynoptic data cannot be validly compared point to point in mapping the soil gas hydrocarbon field because of the varying concentrations over the time span of measurements. The present invention provides a time span sampling protocol that accommodates the natural phenomena responsible for large fluctuations of concentration, and thereby remedies the deficiencies of prior techniques.

Minerals Exploration

In the metals mining industry, tracer gas techniques have been most notably employed in exploration for uranium and for gold. In the case of uranium, the related pathfinder gas is the noble gas radon (Rn-222) arising in the radioactive decay chain of uranium. Although gold itself has no gas phase, it frequently occurs in association with mercury compounds and small amounts of free elemental mercury resulting from biochemical or geochemical reduction of mercury salts. Even though mercury has a low vapor pressure (approximately 0.001 mm Hg), this is sufficient to produce detectable soil gas concentrations.

The variability of soil gas concentration has been widely experienced in uranium exploration—where the techniques have been extensively employed—to the extent that irreproducibility of measurements has led to an attitude of distrust of the technology as other than a supporting but often suspect adjunct to more familiar methods.

Other potential applications of presently employed gas tracer techniques in a variety of other mineral exploration applications here involve considerations similar to those discussed above. These include: mapping phosphate beds based on radon emission from low level uranium content therein; exploration for sulfur deposits in salt domes, based on emission of gaseous sulfur compounds, carbon dioxide, and radon; exploration for geothermal sources; exploration for subsurface water bodies in desert regions based on water vapor emission. All present similar complications with respect to previously unexplained variability in relation to presently employed gas tracer techniques. Even carefully controlled experiments of radon gas concentration over a 13-month period (R. L. Fleischer and A. Mogro-Campero, Geophysical Research Letters, pp. 362–4, May 1979) have led to admitted lack of explanation of the variation and speculations as to in-earth convective cells that our data indicate not to be a correct interpretation.

Evaluation of Pollutant Sources

In the area of toxic materials management, soil gas techniques are applicable in the detection and evaluation of buried substances, either naturally occuring or anthropogenic in nature and not readily detected by other surface techniques.

(i) A prominent example of a naturally occurring hazard is radon emitting into residences, schools and other buildings. Evaluation of large statewide areas to define high and low risk regions can be done using atmospheric sampling techniques to map regional variations in radon emission intensity (G. H. Milly, Mobile Measurement of Radon Concentration in East Coast Terrain, U.S. Environmental Protection Agency Contract No. 68-01-7341, February 1987, Quadrel Research Corporation). As in the case of uranium exploration based on soil gas radon, large variations in emission rate can and do typically occur over a period of several hours. Depending on when the measurements are made, an area actually presenting a substantial threat can appear harmless. Another example of natural pollutants relates to sulfur compounds, and practical concerns of their role in acid rain. Emission rates have been measured employing a large area sampling grid over the eastern United States to assess the fractional contribution of natural sulfur to industrial sulfur dioxide and sulphate loadings of the atmosphere. (D. F. Adams et al., Biogenic Sulfur Emissions in the SURE Region Electric Power Research Institute, EA-1516, Project 856-1, September 1980). However, potentially large temporal variations across the non-simultaneous but serial grid-point measurements were not recognized or accommodated.

(ii) Anthropogenic hazards are represented most pervasively by numerous widespread toxic chemical waste sites where toxic industrial and commercial materials have been dumped and then covered over with earth. Waste site investigations involve various methods of detection and evaluation of the content and area perimeters of subsurface contamination including measurements of volatilized vapors of buried contaminants contained in soil gas. Post-closure monitoring after clean-up may also employ soil gas techniques. Current practice of soil gas mapping entails sequential point to point sampling over an area array. The problems previously cited regarding temporal variation are such that, under certain conditions, misleadingly little or no emission is detectable; and, under favorable conditions for emission, short term variability distorts the true pattern because of asynoptic observations. Similar considerations apply to other anthropogenic hazards such as radon emissions from uranium mill tailing piles.

Summary

In summary, there are numerous examples of economic and public health importance where assessments may be made on the basis of measurements of soil gas either directly, or indirectly through resultant atmospheric concentration; and the utility or even validity of these techniques is readily thwarted by wide variations in emission rates and resultant atmospheric concentration levels. Applicant explains this variation and provides a method for enhanced measuring of soil gas, so as to control planning and scheduling of measurement programs and minimize or eliminate the effect of variability; while providing enhanced comprehension in the analysis of data by recognizing the source of these variations.

SUMMARY OF THE INVENTION

Post-compression method of measuring soil gas concentrations and emissions so as to minimize effects of natural variability and to enhance measurement sensitivity. The method is characterized by defining gravitational acceleration on the surface of the earth induced by the sun and moon, calculating the vertical component of the gravitational acceleration vector and compensating for variation and acceleration due to geographic location; then post-compression measuring of soil gas concentration during periods of maximum soil gas emission. The post-compression method of measuring may be restricted both to the long term (approximately 1–10 days) and the short term (approximately 1–8 hours) for maximum average semi-diurnal gravitational acceleration.

DESCRIPTION OF THE PREFERRED EMBODIMENTS

The fluctuation in soil gas concentration and emission flux rates over relatively short periods of time is a recognized phenomenon that has been previously studied. Much of the work is based on radon as a naturally occurring test gas because it is an ubiquitous and convenient substance for this purpose. These studies have suggested that meteorological factors are responsible for some portion of the variation. Most frequently noted are wind speed, soil temperature and rainfall, and barometric pressure changes (Kramer et al., "Measurements of the Effects of Atmospheric Variables on Radon-222 Flux and Soil Gas Concentrations", The Natural Radiation Environment, Adams and Lowder, eds., 1964; Klusman, R. W. and Webster, J. D., "Meteorological Noise in Crustal Gas Emission Relevant to Geochemical Exploration", J. Geochem. Explor., v. 15, pp. 63–76, 1981; Clements, W. E. and M. H. Wilkening. "Atmospheric Pressure Effects on $^{222}$Rn Transport Across the Earth-Air Interface", J. Geophys. Res., v. 79, no. 33, pp. 5025-29, Nov. 20, 1974). Of these, pressure change may be the most important by inducing a kind of pumping action, drawing soil gas upward and out of the earth during falling pressure and reducing or suppressing emission during increasing pressure. Applicant's experiments have shown however, that meteorological factors fail to explain the frequency, time of occurrence, and magnitude of the observed fluctuations. Rather, applicant's experiments have shown that by far the dominant causal mechanism is the phenomenon known as earth tides.

Earth tides, analogous to ocean tides and atmospheric tides, consist of ellipsoidal deformation of the earth's otherwise normal oblate spheroid shape. The deformation is brought about in response to the gravitational acceleration induced by the earth's principal celestial neighbors—the moon and the sun. As the earth rotates on its axis, and as it progresses on its orbit around the sun (the ecliptic), meanwhile being itself orbited by the moon, the earth is subjected to gravitational pull resulting in a bulge in the direction of the vector sum of the forces of these two external bodies, and a reflectant antipodal bulge. As the earth rotates while progressing in its orbit, the gravitational acceleration is experienced as sweeping over the earth with a vector magnitude and direction dependent on latitude, longitude and elevation above sea level of the point of observation on the earth. The cyclic variation in gravitational acceleration felt at any specified point is aperiodic in that it is not a precise repetition of a wave-like function but displays variations dependent on the ever changing positional and attitudinal relations among the three bodies.

Figure 1:
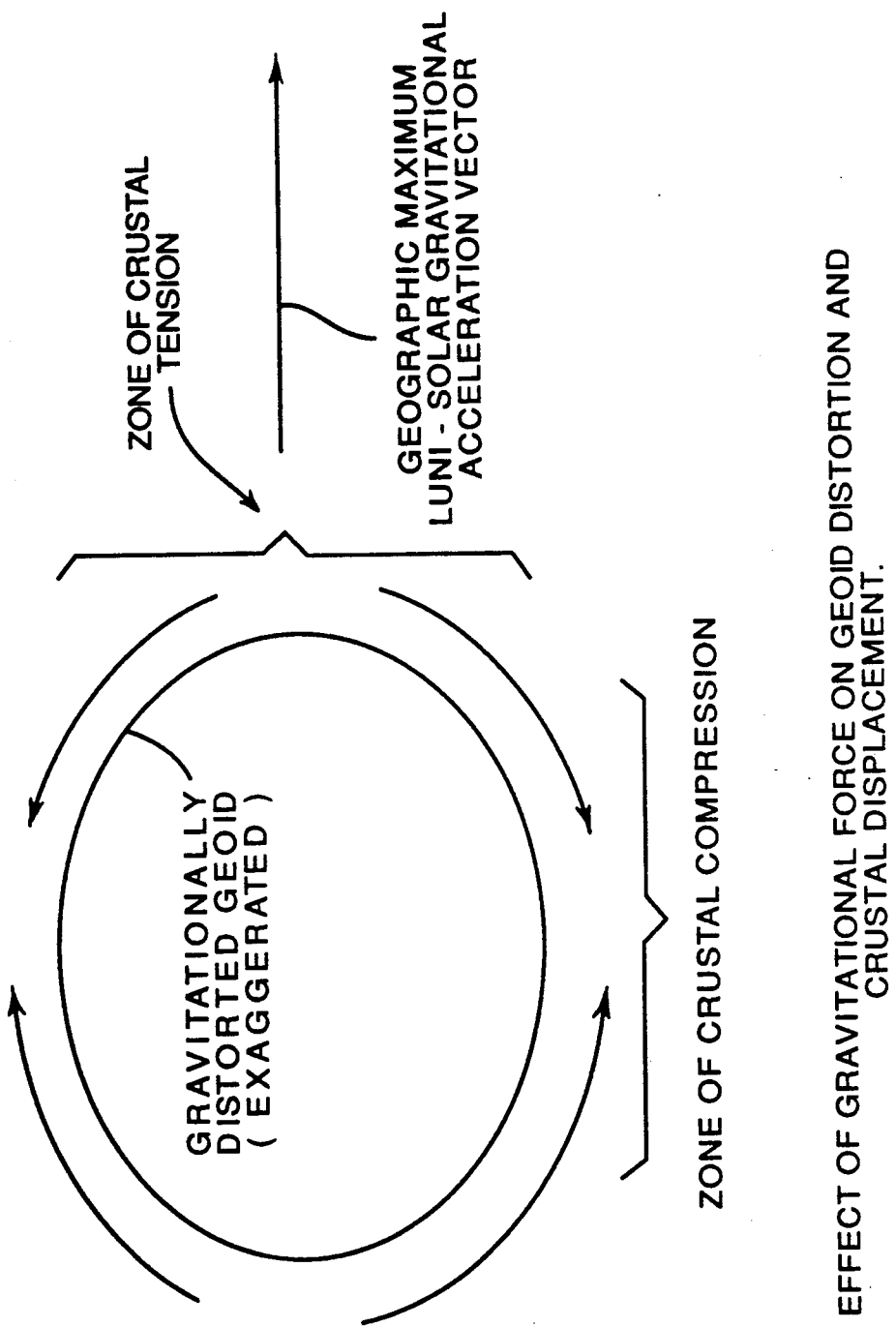
FIG. 1 is a schematic view depicting earth's crustal tension/compression sequence.

The practical result of these interactions is that the region of the earth experiencing maximum acceleration will be subject to crustal tension due to distortional stretching as will its antipodal region, while the intervening areas will experience a compensating collapsing crustal compression (FIG. 1). As the earth rotates, a given geographic point will, therefore, be subjected to alternating tension and compression. Under conditions of tension, the earth's crustal porosity increases, and fractures, fissures and microcracks expand, thereby opening up routes of escape of soil gases from within the earth toward the surface and across the earth-air interface into the atmosphere, while at the same time permitting these routes to be filled with interiorly generated gases as well as inspired volumes of the ambient atmosphere. During the following period of crustal compression, these openings become closed to their minimum levels, thereby expelling the aforementioned soil gases that have entered the open voids. The process of closure is capable of inducing very high gas velocities in the earth contrary to the generally held assumption that vertical gas migration is by molecular diffusion. Our experiments indicate that transport velocities within the earth often are several orders of magnitude (up to 10,000 times) greater than diffusion velocities.

We have found the phenomenon of earth tides, as illustrated below, to be the dominant factor in producing repeated and frequent large fluctuations of soil gas emission flux rate and; that these fluctuations are secondarily modified by meteorological variables. The geologic setting of a particular location is a constant, and so can affect the absolute magnitude and range of variation in soil gas concentrations and emission flux rates, but the fundamental pattern of variation persists.

An understanding of the variation in gravitational acceleration enables improved design of observational programs and interpretation of resultant data. For maximum sensitivity of detecting buried sources of soil gas constituents, it is advantageous to make measurements during periods of maximum emission flux rate and to avoid periods when emission is at a minimum or suppressed entirely. It is, therefore, essential to know the time of occurrence and duration of periods of maximum emission in order to plan more precisely the timing of short term observations or the scheduling of more extended time-averaged measurements. The present invention enables such determinations and thereby enhances control of planning and scheduling of soil gas measurements so as to optimize their validity and effectiveness. In order to practice this invention, one must (1) define by calculation and prediction gravitational acceleration as a function of time for a given location and (2) specify periods of both maximum emission and minimum emission within the curve of variation of gravitational acceleration. Because of the complexity and tediousness of the calculations, the calculation of tidal force can be done most conveniently by computer methods. These calculations can be done by means of previously published methods (Longman, I. M., "Formulas for Computing the Tidal Accelerations Due to the Moon and the Sun", J. Geophys. Res., v. 64, no. 12, pp. 2351-2355, December 1959; H. N. Pollack, "Longman Tidal Formulas: Resolution of Horizontal Components", J. Geophys. Res., v. 78, no. 14, pp. 2598-2600, May 10, 1973). Innovation in this invention consists in the manner in which computations of gravitational force are employed as one component of a system of control and analysis of measurement programs related to soil gas concentration and emission flux rates. The second question having to do with specification of favorable measurement periods within the tidal acceleration cycle, i.e., the relationship between variations in gravitational force and variations in emission rates, is discussed in the following section.

Experimental Results

Experimental data are presented below to illustrate the effects of tidal forces as described above and further to confirm reduction to practice of this invention. The data consist of several categories:

(1) examples of calculated gravitational acceleration curves depicted on several time scales as used in planning and control of observational programs,
(2) examples of variation in atmospheric concentrations related to phase of the tidal phenomenon,
(3) examples of measured emission flux rates related to phase of the tidal phenomenon,
(4) examples of practical application of radon surveys to the detection of anomalies relatable to uranium mineral deposits,
(5) examples of the detection of atmospheric mercury anomalies, and
(6) examples of detection of buried toxic wastes.

Figure 2:
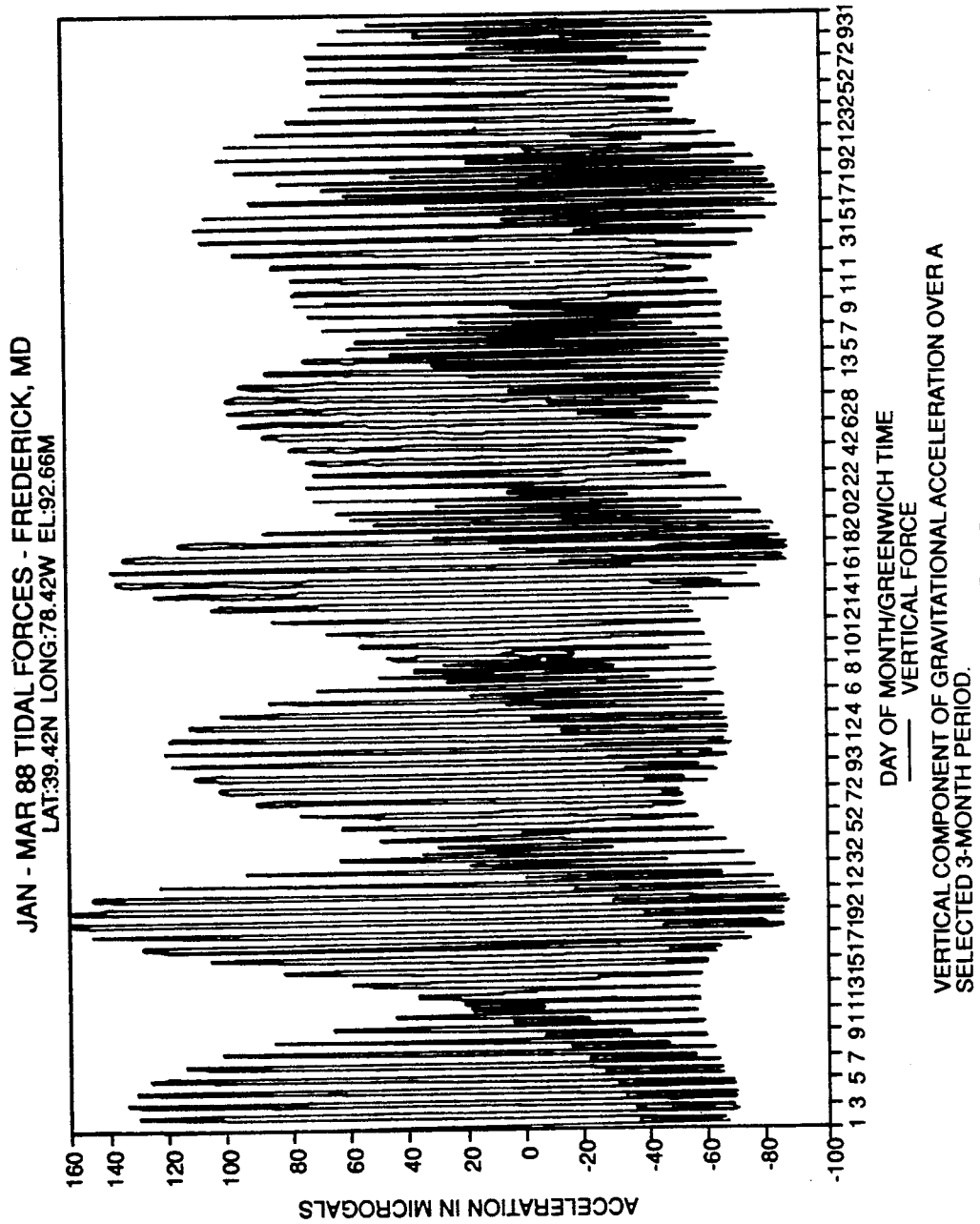
FIG. 2 is a graph depicting the vertical component of gravitational acceleration over a selected 3-month period.
Figure 3:
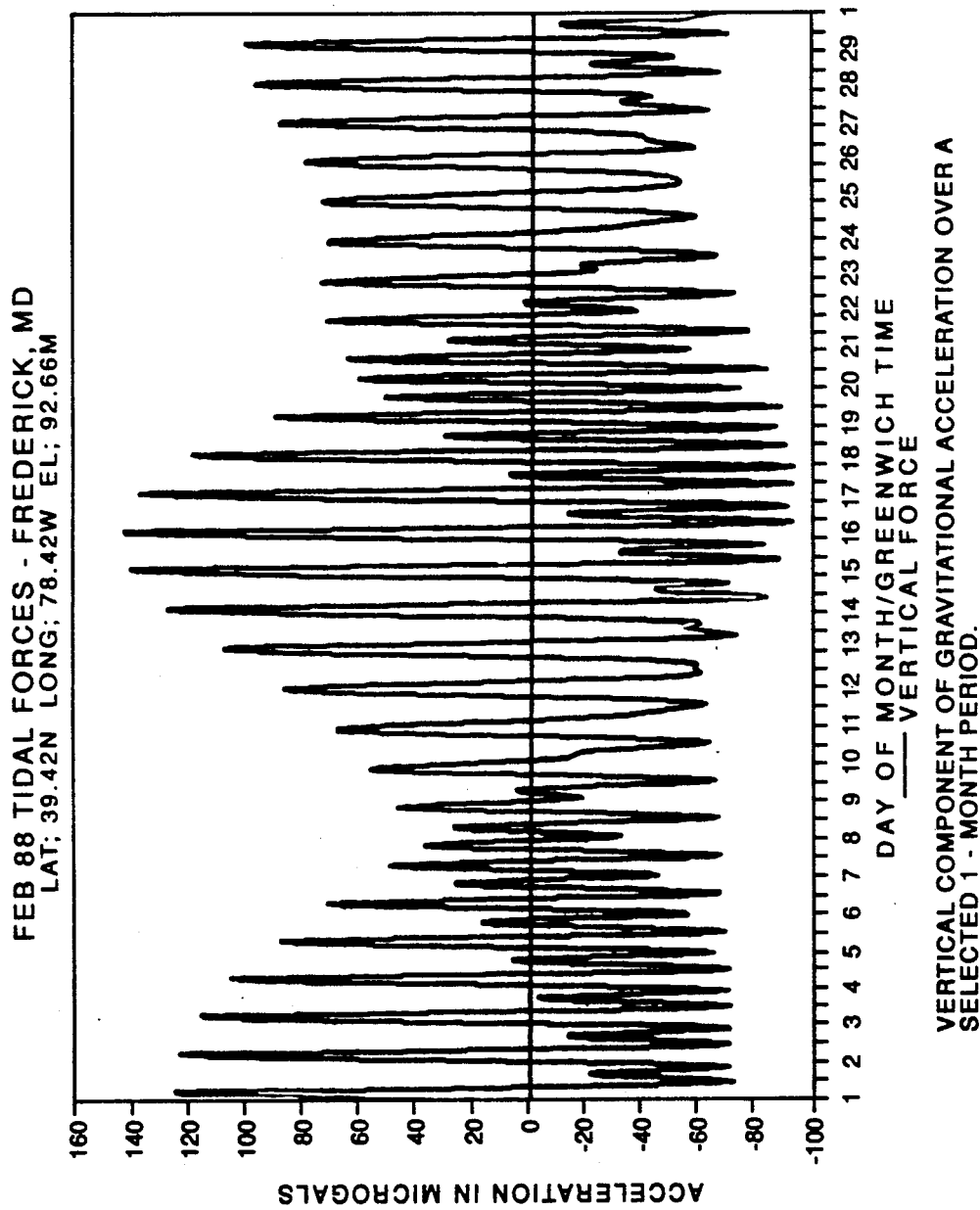
FIG. 3 is a graph depicting the vertical component of gravitational acceleration over a selected 1-month period.
Figure 4:
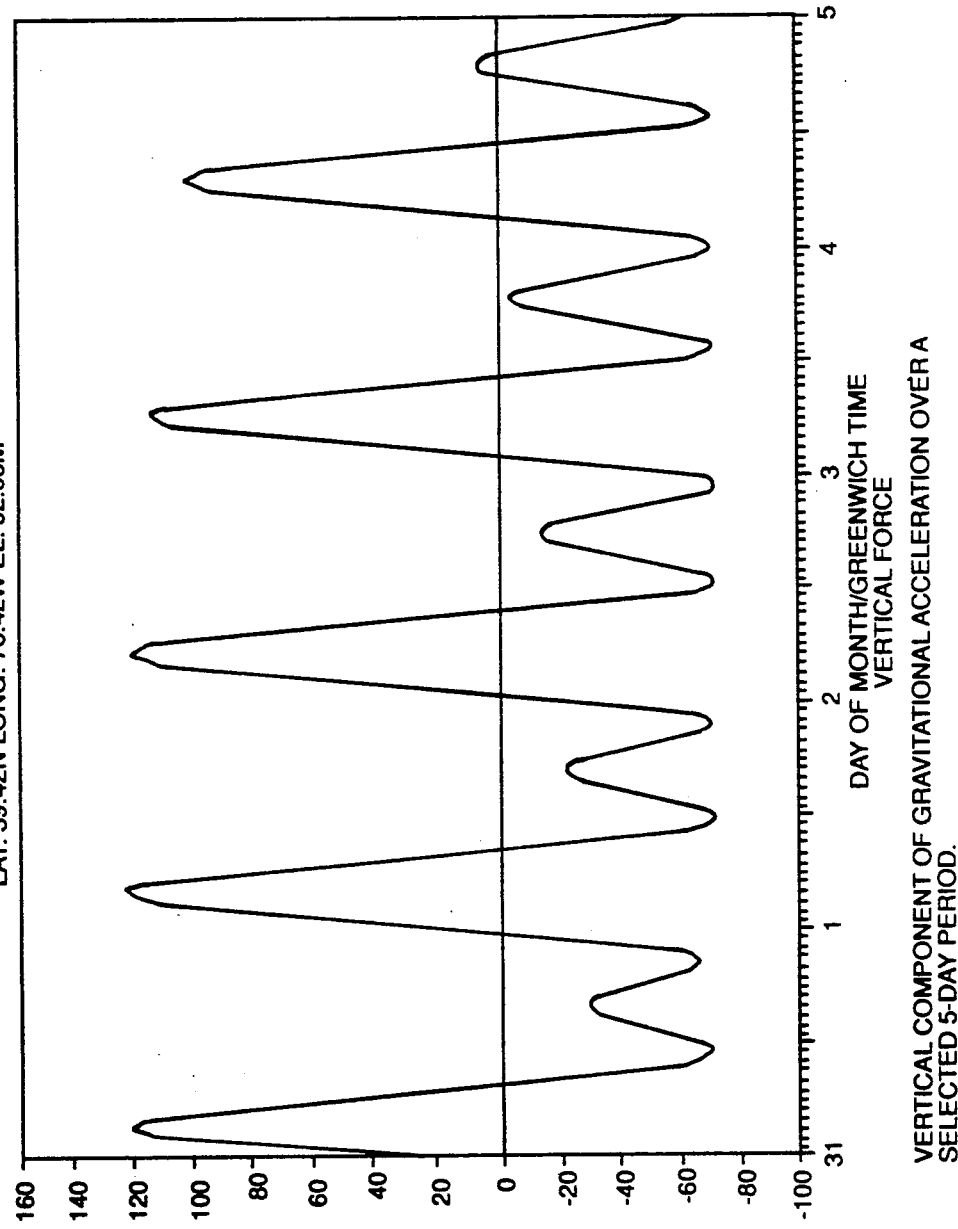
FIG. 4 is a graph depicting the vertical component of gravitational acceleration over a selected 5-day period.

Examples of calculated gravitational acceleration curves are shown in FIGS. 2, 3 and 4.

FIG. 2 illustrates the overall form of variation when viewed over an arbitrarily chosen period of three months. Only the vertical component of the lunar-solar gravitational acceleration is shown, i.e., the component perpendicular to the earth's surface at the location for which calculations are made. Applicant has found the vertical component to be the determining factor in affecting soil gas emission flux rate. It will be noted that the outer envelope of the cyclic function shown corresponds closely to the lunar or anomalistic month of 27.55 days and is well known as the $M_1$ period of the tidal function. Favorable times for soil gas measurement are those corresponding to the envelope maximum as is demonstrated below.

FIG. 3 shows the variation in the vertical component of gravitational acceleration on a more expanded scale corresponding to a period of one month. It will be seen that the acceleration intensity varies within the lunar month with maximum near full and new moon resulting in spring tides, and minimum at first and last quarters (in the dark) of the moon resulting in neap tides. The average time of 14.76 days between spring tides illustrates the fortnightly interval from full moon (in opposition) to new moon (in conjunction) and is distinguished from the lunar fortnightly interval of 13.66 days which is the time for the moon to change declination from zero to maximum and back to zero.

Further expansion of the time scale in FIG. 4 shows the vertical component of gravitational acceleration over a range of five days centered on a lunar monthly maximum. This period is chosen for further examination because it corresponds to the most favorable period within an acceptably favorable period of about ten days for soil gas and related atmospheric observations. In this display, it will be seen that there is a semi-diurnal variation corresponding to the $M_2$ lunar tidal mode, with a period of 12 hrs. 25 mins. due to rotation of the earth and a diurnal period of 24 hrs. 50 mins. due to rotation of the earth and declination of sun and moon.

For short term soil gas observations, it is shown below that the semi-diurnal maxima within the lunar month maxima at full and new moon are important determinants for effective measurement of soil gas emissions. For longer term averaging measurements over a period of several days, the monthly maxima correspond to periods of maximum emission flux rates.

The relationship between variation in gravitational acceleration as described above and the corresponding soil gas behavior can be illustrated by several kinds of data. Atmospheric concentrations of gases emitted from the soil are proportional to the rate at which the gases are emitted, although the actual concentrations are additionally influenced by meteorological and terrain conditions. Consequently, when emission is low, air concentrations are low and vice versa. This feature has been repeatedly observed. By making a series of measurements under comparable meteorological conditions over the same piece of terrain at various times in the tidal cycle, the effect of earth tides on emission flux rate can be demonstrated. In a more direct way, emission flux rate can be measured continuously over time through various phases of the tidal cycle, thus permitting delineation of a relationship between tidal acceleration and emission rate that is less dependent on meteorological considerations. Operational applications of both kinds have been made, examples of which are given below, based on naturally occurring radon (Rn-222) as an ubiquitous and convenient chemically inert test soil gas arising in the radioactive decay chain from uranium.

As a result of the discoveries made relating emission to tidal cycle, extensive exploration projects have been conducted using radon as a tracer gas to discover uranium ore bodies. Using this method of tidal planning and control some 200,000 radon observations have been made in the Western United States over an area of some 70,000 square miles, and in Canada and France. Ore bodies have been discovered by this method and over 34 million pounds of uranium reserves proven by development drilling on the initial discovery.

Operational examples follow involving both atmospheric concentration measurements and the direct measurement of emission flux rates.

EXAMPLE NO. 1

Atmospheric Concentrations Downwind of a Soil Gas Emission Source

Measurements were made of the daughter products of radon in the low level atmosphere by vacuum collection on micropore filters, followed by counting alpha radiation with an alpha scintillation/photomultiplier detection and counting system. The measurements were made under nighttime conditions of near-surface temperature inversion and low wind speed in an area of west central New Mexico. Profiles of alpha activity were measured on nine different nights along a 15 mile route subject to katabatic airflow and under similar meteorological conditions. The peak activity measured along the profile was projected back to the source 10 miles upwind to obtain a relative measure of emission intensity. The slight variation in wind speed among experiments (range 1.8–3.9 mph) was taken into account in calculating the time at which the emission occurred that resulted in the measured peak. Nearly all the measurements were made during the period of one of the two monthly tidal force maxima, but with different projected emission times in relation to the semi-diurnal cycle.

The relative emission intensities were averaged according to phases in the earth tidal compression period with the following results:

| Earth Tidal Phase | Average Relative Emission Intensity |
| --- | --- |
| Compression | 487 |
| Post-Compression | 2,159 |
| Pre-Compression | 788 |

Figure 5:
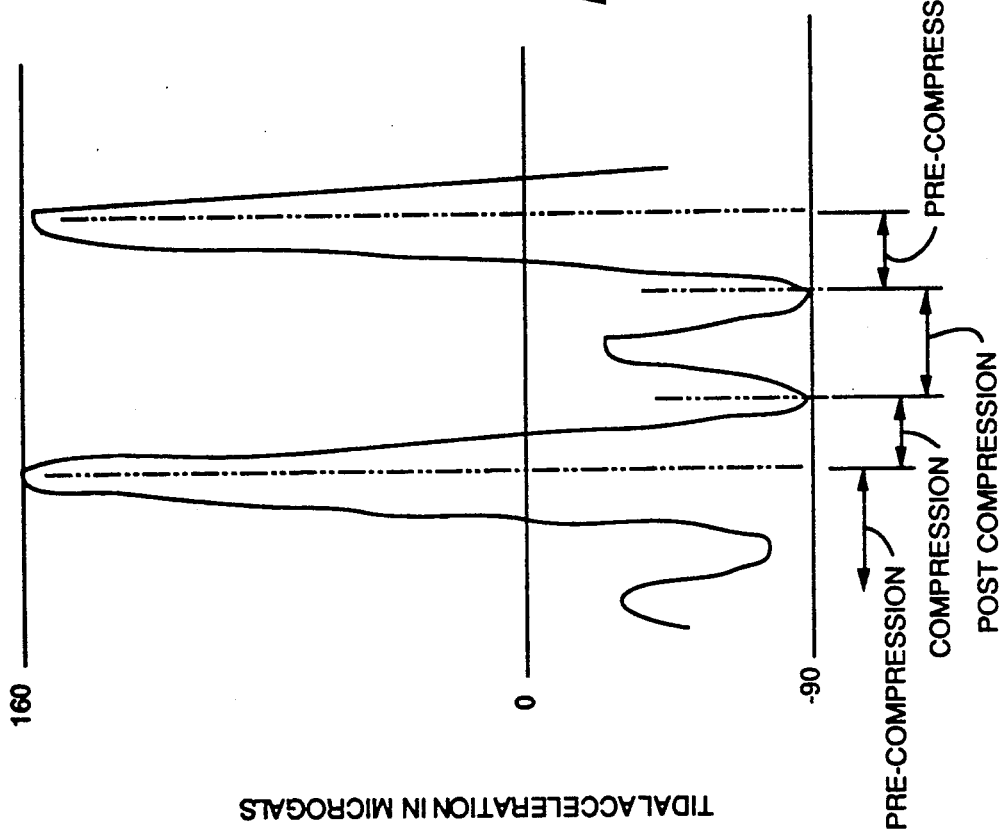
FIG. 5 is a graph depicting the typical tidal acceleration curve depicting the earth crustal compression sequence.

The results are shown against the tidal curve in FIG. 5 where it may be observed that the maximum emission flux rate occurs in the post-compression phase of the tidal force cycle at a time interval of 7 to 14 hrs. after the principal tidal force peak. Emissions prior to and after the post-compression phase are substantially reduced.

EXAMPLE NO. 2

Atmospheric Concentrations in the Vicinity of a Soil Gas Emission Source

A further series of experiments was conducted to illustrate the effects of short term variation in the gravitational force. Atmospheric radon daughter ions were measured in the immediate vicinity of the same source as in Example No. 1 above, over a span of hours involving the semi-diurnal variation. A total of 13 experiments were done, each on a different night and under comparable low wind and inversion conditions. On each experiment, 30 to 50 samples were taken. The time at which the maximum concentration in each experiment was measured was determined as a lag past the preceding semi-diurnal peak. The relative emission intensities represented by the peak concentrations were averaged according to time intervals with the following results:

| Time Past Dirunal Tidal Peak, Hours | Average Relative Emission Intensity |
|---|---|
| 0–7 | 293 |
| 7–14 | 1,517 |
| 14–23 | 454 |

The pattern of variation is similar to that of Example No. 1, the values here being consistently in the range of 60% to 70% of those in the preceding example, the difference in magnitude being due to differences in location of measurement and consequent differences in age of the atmospheric radon cloud and development of daughter ions. Hence, the pattern of FIG. 5 is applicable to this example, and nearly identical with a 65% scale factor on emission intensity.

EXAMPLE NO. 3

Figure 6:
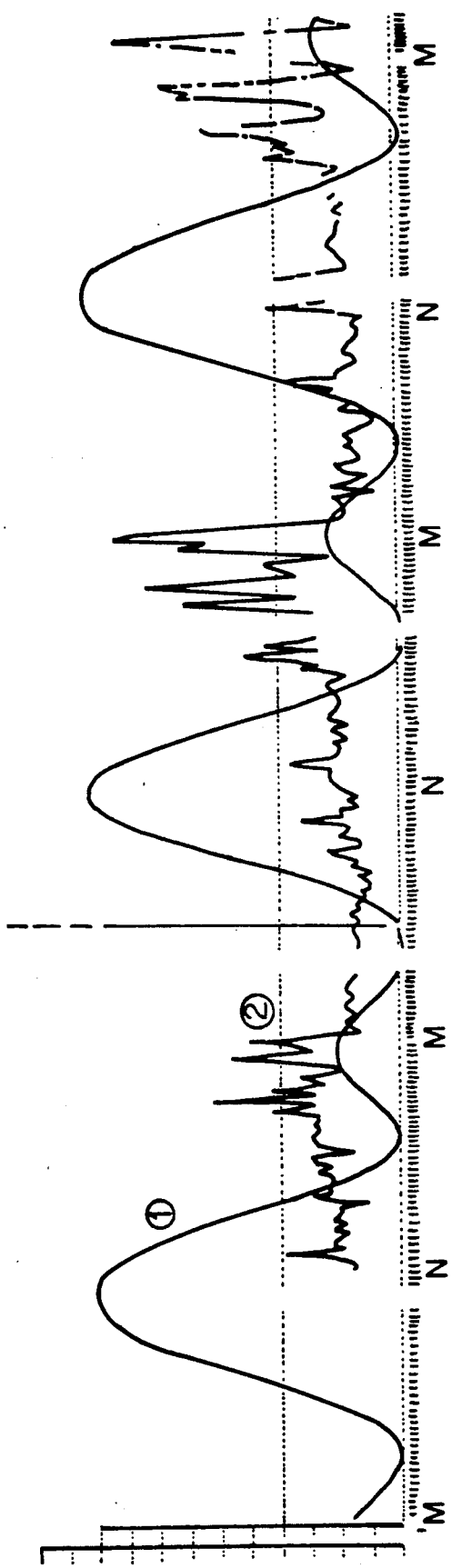
FIG. 6 is a graph depicting three-day time series of emission flux rate and gravitational acceleration intensity.

A Three-Day Time Series of Emission Flux Rate Over a Naturally Occurring Radon Source In contrast to the two preceding examples based on atmospheric concentrations, direct evidence of the dependence of emission flux rate on gravitational acceleration and the resultant earth tidal response was obtained by making serial observations of emission flux at a fixed point. These results may then be compared with the calculated curve of gravitational force. Measurements of radon emission flux rate were made in a uraniferous area of central Wyoming; consecutive 15 minute samples were taken over a period of three days at a time of a fortnightly peak in tidal acceleration. The comparison curves of flux and acceleration are shown in FIG. 6. The peaks in emission rate following each semidiurnal maximum tidal force are seen to occur in the post-compression phase encountered in the two preceding examples, and fall within the same period of approximately 7 to 14 hours following the tidal peak. The spiked form of the emission rate is a result of stick-slip phenomena within the earth as rock adjusts in a succession of slips to the tidal stresses. The relatively high intervening "background" emission rates are due to elevated concentrations of uranium in the surface layer of the earth.

The technique of measurement involved a closed container placed on the earth's surface so that external wind effects were eliminated. Suggestions in the literature that higher temperatures result in gas expansion and increased emission rates were found to be without effect inasmuch as the maximum emissions were observed in the pre-midnight hours when surface temperatures were lowering. The principal meteorological variable of concern is barometric pressure. However, the regularity of the diurnal emission maximum is not consistent with typical variations in barometric pressure of a significant magnitude, nor with the observed pressure record which showed little variation. These results support the cycle of gravitational acceleration and the resultant earth tidal force as a controlling factor in the application of soil gas measurement techniques.

This example shows that even short term soil gas emission rate is strongly dependent on time within the luni-solar cycle. For long term sample collection periods of several days, it is sufficient to choose a time when peak force within the semi-lunar month is high. The resultant averaging process will include the intervening short period low values but nevertheless give rise to maximum integrated flux rates. For short time measurements, i.e., instantaneous to averaging over several hours duration, it is important to make observations within the post-compression period of about 7 to 14 hours following the individual maximum.

EXAMPLE NO. 4

Figure 7:
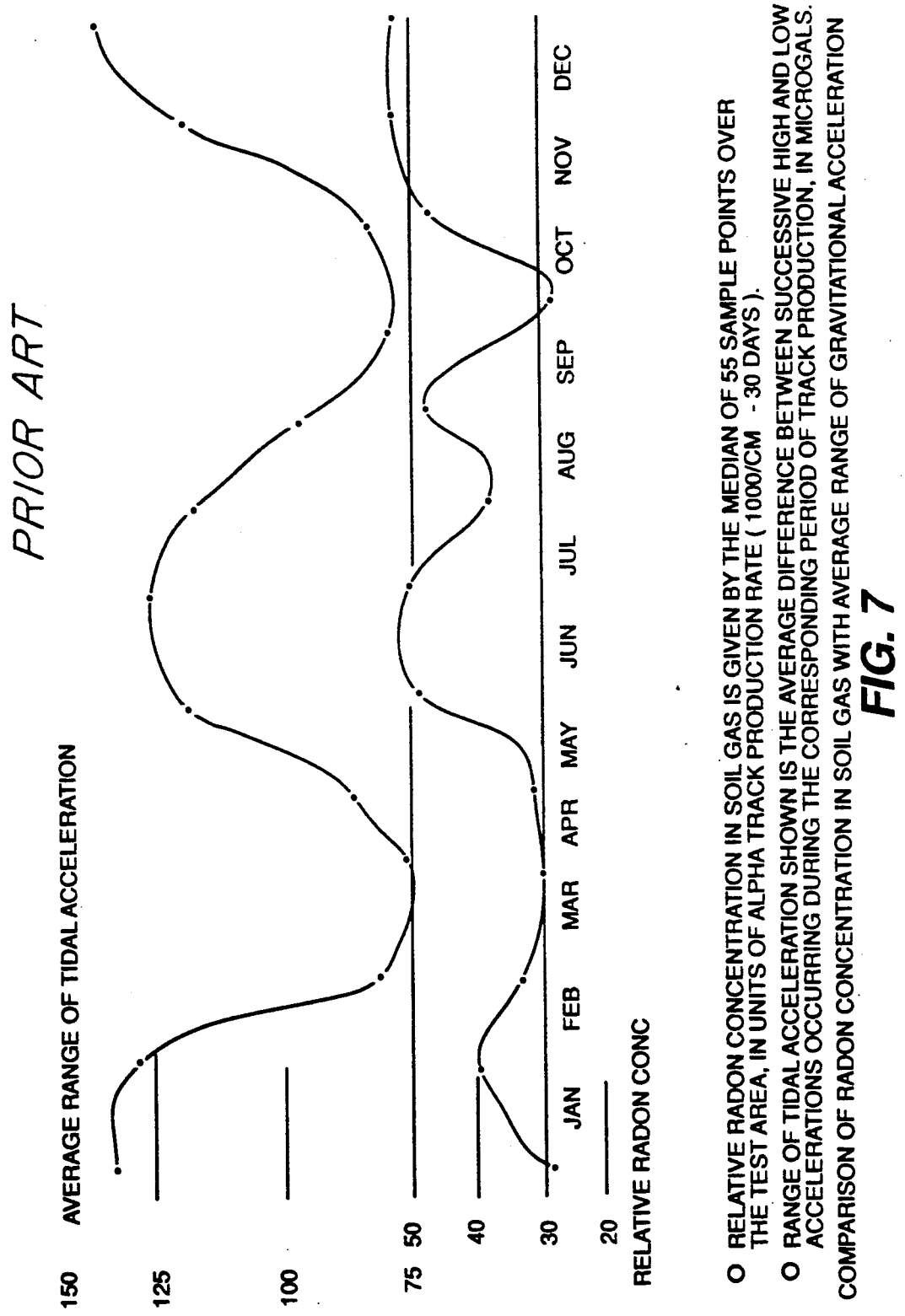
FIG. 7 is a prior art graph depicting comparison of radon concentration in soil gas with average range of gravitational acceleration.

A Thirteen-Month Time Series of Soil Gas Concentration Over a Naturally Occurring Radon Source As mentioned above under Description of the Prior Art—Minerals Exploration, a thirteen month series of soil gas concentration of radon conducted by Fleischer and Mogro-Campero showed time variations that they were unable to explain. Their results are shown in FIG. 7 alongside applicant's calculation of the intensity of gravitational acceleration. Even though only monthly values are plotted, the parallelism between the curves is supportive of applicant's findings concerning the dominant role of tidal forces. This is especially noteworthy inasmuch as all other environmental or meteorological variables are neglected in the comparison.

EXAMPLE NO. 5

Evaluation of a Buried Toxic Chemical Waste Site

A toxic waste site in Massachusetts was studied by measuring at several points the emission of hydrocarbon vapors of the various buried chemical substances. Control of the measurement program was done in accordance with the methods of this invention. Specifically, an eight day period of collection of emissions was centered on a fortnightly tidal maximum. Analysis of the samples revealed the presence of eight contaminants: 1,1-dichloroethylene; ethyl benzene; 1,1,1-trichloroethane; benzene, toluene; chloroform; tetrachloroethylene; and 1,2-dichloropropane. Of these compounds, two (1,1-dichloroethylene and ethyl benzene) had been previously identified by the site owner through drilling and sub-surface soil sampling. Subsequent to the emission measurements further drilling was undertaken by the owner and three more of the eight emissions confirmed (1,1,1-trichloroethane; benzene; chloroform) and an additional one (toluene) suspected, but not positively identified. The problem of pre-determining depth from which to draw samples when the depth of the various toxics is unknown renders exhaustive recovery uncertain. In contrast, contaminants occurring at all lower levels, are sensed by the emission techniques employed in conjunction with tidal scheduling.

APPLICATIONS

Summarizing the foregoing discussion and experimental results, the invention described here consists of a method of measuring soil gas concentrations, soil gas emission flux rates, and atmospheric concentrations of soil gases, so as to minimize the effects of natural variability in these quantities; and obtaining a higher degree of observational sensitivity by measuring during maximal periods of emission and concentration; and thereby obtaining a high degree of reproducible results. Accomplishment of this method of control is based on calculation of the time function of gravitational acceleration felt at a point on the earth in response to the sun and the moon; including the conduct of long time averaged measurements during fortnightly periods of high acceleration; and the conduct of short time measurements during the post-compression phase of the semi-diurnal cycle within a semi-monthly maximum period.

Since the method of control constituting this invention applies to the movement and emission of any gases from within the earth, it is relevant to an array of applications based on measurements of soil gas concentrations, emissions and resultant atmospheric concentrations.

Without limiting the application of this invention, examples are given below in which soil gas techniques are enhanced by practice of this invention:

a) Mineral exploration for uranium based on atmospheric concentrations and/or emission flux rates of gaseous radon and/or helium.

b) Mineral exploration for mercury, gold and other precious and base metals geochemically associated with mercury or mercury compounds, based on atmospheric concentrations and/or emission flux rates of mercury vapor and/or associated volatile compounds such as, for example, those of arsenic and antimony.

c) Mineral exploration for oil and gas based on atmospheric concentrations and/or emission flux rates of a spectrum of hydrocarbon compounds, and/or of radon and helium haloes.

d) Exploration for sub-surface sulfur deposits, especially in salt domes, based on atmospheric concentrations and/or emission flux rates of hydrogen sulfide, sulfur dioxide and carbon dioxide that arise in the process of sulfur deposition; and radon arising from uranium precipitated by chemical reduction from the overlying ground water due to passage of the aforementioned sulfur compounds.

e) Exploration for sources of sub-surface water bodies in desert and arid regions based on atmospheric concentrations and/or emission flux rates of water vapor.

f) Exploration for geothermal sources based on anomalously high emissions of associated volatile compounds such as, for example, boranes.

g) Exploration for phosphate minerals and mapping of buried phosphate beds based on typically high geochemical association of uranium and resultant radon emissions.

h) Exploration for and mapping of gaseous methane as a fuel source occurring in association with coal beds.

i) Exploration for and mapping of sub-surface coal deposits based on emission of methane.

j) Any and all other mineral exploration applications where a gas phase substance is or can be associated with the mineral target.

k) Area mapping of the regional distribution of radon emission intensity in relation to environmental concerns about radon concentrations in homes, schools, and other buildings, as a means of identifying threat areas for more detailed follow-up inside structures.

l) Evaluation of radon emmision levels on land parcels under consideration for sale, purchase, or construction thereon, with regard to potential environmental threat inside buildings.

m) Evaluation of buried toxic chemical waste sites to include identification of pollutants by recovery of vapor emissions without surface intrusion; mapping of extent, periphery and areal distribution of relative intensity of the identified pollutants based on emission of pollutant vapors; and the detection, tracing and mapping of leachate plumes of contaminants based on emissions of pollutants and/or radon, where radon emissions permit mapping of preferred leachate routes such as rock fractures.

n) Long term post-closure monitoring of toxic chemical waste sites following waste site remediation procedures in order to monitor variations in subsurface pollutant beyond the confines of the remediation site.

o) Evaluation and monitoring of uranium mill tailings piles for radon emissions as a polluting constituent of the atmosphere, based on emission flux rates and atmospheric concentrations.

p) A means of providing improved, more accurate and representative determinations of source strengths of both natural and anthropogenic buried substances in the evaluation of local air pollution exposure, potential and effects.

q) A means of providing improved, more accurate and representative determinations of source strengths of sulphur compounds of natural origin as opposed to industrial sources, in connection with the evaluation of acid rain effects and policy.

r) A method of experimental control in the prediction of earthquakes based on fluctuations of radon concentration in response to stress buildup, by providing a base curve of tidally induced radon concentrations against which anomalous deviations can be better judged in relation to earthquake potential.

I claim:

1. Post-compression method of measuring soil gas concentration and emission flux, so as to minimize effects of natural variability and to enhance measuring sensitivity comprising:

a) observing gravitational acceleration on the surface of the earth in the form of earth tides as defined by crustal tension and compression and as induced by the sun and moon;

b) compensating for variation in acceleration due to geographic location of said observing;

c) locating said crustal tension in the form of a bulge on the surface of the earth, said bulge extending in the direction of the vector sum of the forces of the sun and moon; and d) post-compression measuring of soil gas concentration and emission flux rate during periods of maximum soil gas emission.

2. Post-compression method of measuring soil gas concentration and emission flux as in claim 1, including:

e) restricting said post-compression measuring on a long term basis to approximately 1 to 10 days for measuring average post-compression soil gas concentration and emission flux rate, during periods of maximum average semi-diurnal gravitational acceleration occurring within the lunar month; and f) further restricting said post-compression measuring on a short term basis to approximately 1 to 8 hours for measuring soil gas concentration and emission flux rate during the post-compression phase of a single semi-diurnal gravitational acceleration maximum occurring within the lunar month.

3. Post-compression method of measuring soil gas concentration and emission flux as in claim 2, said measuring of soil gas flux including adjacent measuring of atmospheric concentration of said soil gas.

4. Post-compression method of measuring soil gas concentration and emission flux as in claim 2, wherein said soil gas is in the form of gaseous radon 5. Post-compression method of measuring soil gas concentration and emission flux as in claim 2, wherein said soil gas is helium.

6. Post-compression method of measuring soil gas concentration and emission flux as in claim 2, wherein said soil gas is hydrocarbon from oil and gas deposits.

7. Post-compression method of measuring soil gas concentration and emission flux as in claim 2, wherein said soil gas is mercury vapor.

8. Post-compression method of measuring soil gas concentration and emission flux as in claim 2, wherein said soil gas consists of volatile inorganic compounds of boron, arsenic and antimony.

9. Post-compression method of measuring soil gas concentration and emission flux as in claim 2, wherein said soil gas consists of volatile organic compounds emitted from buried toxic wastes.

10. Post-compression method of measuring soil gas concentration and emission flux as in claim 2, wherein said soil gas consists of semi-volatile organic compounds emitted from buried toxic wastes.

11. Post-compression method of measuring soil gas concentration and emission flux as in claim 2, wherein said soil gas is acid fumes.

12. Post compression method of measuring soil gas concentration and emission flux as in claim 2, wherein said soil gas is sulfur compounds.

13. Post-compression method of measuring soil gas concentration and emission flux as in claim 2, wherein said soil gas is carbon dioxide.

14. Post-compression method of measuring soil gas concentration and emission flux as in claim 2, wherein said soil gas is water vapor.

15. Post-compression method of measuring soil gas concentration and emission flux as in claim 2, wherein said soil gas is of natural origin.

16. Post-compression method of measuring soil gas concentration and emission flux as in claim 2, wherein said soil gas is of anthropogenic origin.

17. Post-compression method of measuring soil gas concentration and emission flux as in claim 2, including compensating for variation in acceleration due to geographic setting.

* * * * *